(12) United States Patent
Li et al.

(10) Patent No.: US 10,521,436 B2
(45) Date of Patent: Dec. 31, 2019

(54) SYSTEMS AND METHODS FOR DATA AND INFORMATION SOURCE RELIABILITY ESTIMATION

(71) Applicant: Baidu USA, LLC, Sunnyvale, CA (US)

(72) Inventors: Yaliang Li, Buffalo, NY (US); Nan Du, Palo Alto, CA (US); Yusheng Xie, Campbell, CA (US); Wei Fan, Sunnyvale, CA (US)

(73) Assignee: Baidu USA LLC, Sunnyvale, CA (US)

( * ) Notice: Subject to any disclaimer, the term of this patent is extended or adjusted under 35 U.S.C. 154(b) by 381 days.

(21) Appl. No.: 15/207,434

(22) Filed: Jul. 11, 2016

(65) Prior Publication Data
US 2018/0011856 A1 Jan. 11, 2018

(51) Int. Cl.
| | |
|---|---|
| G06F 16/2457 | (2019.01) |
| G16H 50/20 | (2018.01) |
| G06F 16/2458 | (2019.01) |
| G16H 40/63 | (2018.01) |
| G16H 50/30 | (2018.01) |
| G16H 70/60 | (2018.01) |

(52) U.S. Cl.
CPC .... *G06F 16/24578* (2019.01); *G06F 16/2462* (2019.01); *G16H 40/63* (2018.01); *G16H 50/20* (2018.01); *G16H 50/30* (2018.01); *G16H 70/60* (2018.01)

(58) Field of Classification Search
CPC ....................................................... G06F 17/18
USPC ....................................................... 702/179
See application file for complete search history.

(56) References Cited

U.S. PATENT DOCUMENTS

| | | | | |
|---|---|---|---|---|
| 7,610,313 | B2* | 10/2009 | Kawai | ............... G06F 17/30705 |
| 8,019,582 | B2 | 9/2011 | Iliff | |
| 2001/0044795 | A1* | 11/2001 | Cohen | ............... G06F 17/30699 |
| 2003/0037034 | A1* | 2/2003 | Daniels | ............... G06Q 10/087 |
| 2004/0093331 | A1* | 5/2004 | Garner | ................... G06N 5/022 |
| 2005/0055357 | A1* | 3/2005 | Campbell | ................ G06F 8/61 |

(Continued)

OTHER PUBLICATIONS

Pearl, "Probabilistic Reasoning in Intelligent Systems",1988, (10 pgs).

(Continued)

*Primary Examiner* — Jay A Morrison
*Assistant Examiner* — Ken Hoang
(74) *Attorney, Agent, or Firm* — North Weber & Baugh LLP

(57) ABSTRACT

Presented are systems and methods that estimate the strength of a relationship between elements gathered from online and/or offline information sources by estimating the trustworthiness both of the gathered data and the information sources from which the data originates. In one exemplary application, the relatedness between co-occurring symptom and disease terms collected from information sources, such as health-related online databases, is iteratively evaluated based on the trustworthiness of symptom-disease pairings and the trustworthiness of the information sources themselves. In various embodiments of the present disclosure, an objective function is used to extract a knowledge base that aids in identifying a potential relationship between a set of given symptoms provided by a user of an online healthcare service and co-occurring disease terms, such that a likely disease may be inferred from the set of symptoms.

20 Claims, 6 Drawing Sheets

(56) References Cited

U.S. PATENT DOCUMENTS

| | | | |
|---|---|---|---|
| 2012/0136853 A1* | 5/2012 | Kennedy | G06F 17/30038 707/723 |
| 2013/0310653 A1 | 11/2013 | Zillner | |
| 2014/0101219 A1 | 4/2014 | Tang | |
| 2014/0181214 A1 | 6/2014 | Price | |
| 2015/0006492 A1* | 1/2015 | Wexler | G06F 17/30554 707/694 |
| 2015/0012472 A1 | 1/2015 | Liang | |
| 2016/0078184 A1 | 3/2016 | Konerman | |
| 2016/0253370 A1* | 9/2016 | Song | G06F 9/524 707/704 |

OTHER PUBLICATIONS

Heckerman, "A Tractable Inference Algorithm for Diagnosing Multiple Diseases", 1990, (9 pgs).
Jaakkola et al., "Variational Probabilistic Inference and the QMR-DT Network", 1999, (32 pgs).
Murphy et al.,"Loopy Belief Propagation for Approximate Inference", 1999, (9 pgs).
Ng et al.,"Approximate inference algorithms for two-layer Bayesian networks", 2000, (7 pgs).
Jernite et al., "Discovering Hidden Variables in Noisy-Or Networks using Quartet Tests", 2013, (9 pgs).
Halpern et al., "Unsupervised Learning of Noisy-Or Bayesian Networks", 2013, (10pgs).
Non-Final Office Action dated Mar. 15, 2019, in U.S. Appl. No. 15/215,513, (20 pgs).
Response filed Jun. 17, 2019, in U.S. Appl. No. 15/215,513, (20 pgs).
Non-Final Office Action dated Mar. 7, 2019, in U.S. Appl. No. 15/207,445, (37 pgs).
Response filed Jun. 7, 2019, in U.S. Appl. No. 15/207,445, (16 pgs).
Non-Final Office Action dated Sep. 3, 2019, in U.S. Appl. No. 15/207,445, (40 pgs).
Final Office Action dated Sep. 13, 2019, in U.S. Appl. No. 15/215,513, (11 pgs).
Resposne filed Nov. 13, 2019, in U.S. Appl. No. 15/215,513, (13 pgs).

* cited by examiner

400

SYSTEMS AND METHODS FOR DATA AND INFORMATION SOURCE RELIABILITY ESTIMATION

BACKGROUND

A. Technical Field

The present invention relates to computer processing and, more particularly, to systems, devices, and methods to increase computational efficiency of estimating the strength of a relationship between elements.

B. Description of the Related Art

Booming online healthcare Question and Answer services puts the global online healthcare service industry is on a map to become a billion-dollar industry. As health-related websites, such as medhelp.org in the US and xywy.com in China, allow users to search readily available health-related information online, especially the younger generation increasingly seeks to educate itself about health issues prior to—and oftentimes instead of—visiting a doctor's office. While information from different online sources is not equally trustworthy, a recent report shows that tens of millions of health-related queries are searched every day on Baidu's search engine. The xywy.com website, for example, has millions of registered users and hundreds of thousands of registered doctors. In order to provide high-quality online healthcare services, the ability to extract co-occurring symptom and disease terms from online documents to determine the relation between a symptom and a disease is of significant importance. Therefore, in order to infer, for example, a likely disease from a set of given symptoms, it would be desirable to have systems and methods that can evaluate the relatedness of the co-occurring symptom-disease terms, while, at the same time, evaluating their trustworthiness as well as the trustworthiness of their sources.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

FIGURE ("FIG.") 1 illustrates an exemplary system for estimating a strength of a relationship between elements, according to various embodiments of the present disclosure.

DETAILED DESCRIPTION OF THE PREFERRED EMBODIMENTS

Figure 1:
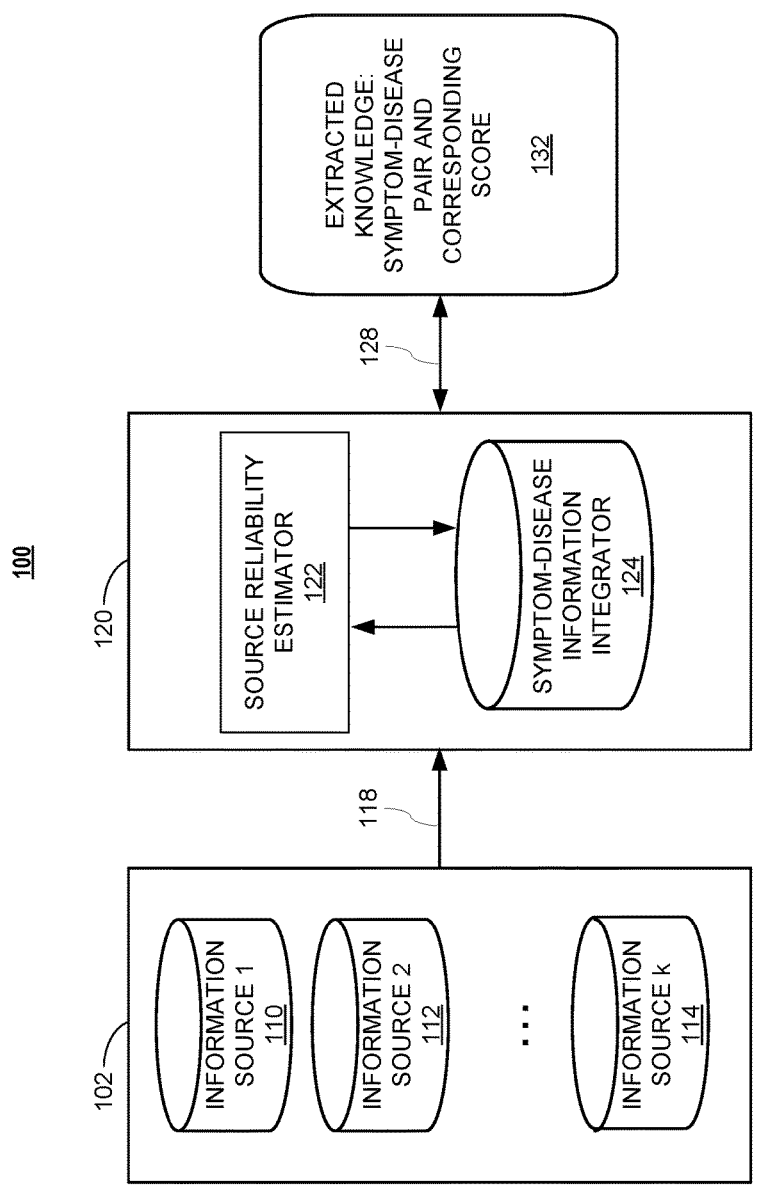

In the following description, for purposes of explanation, specific details are set forth in order to provide an understanding of the invention. It will be apparent, however, to one skilled in the art that the invention can be practiced without these details. Furthermore, one skilled in the art will recognize that embodiments of the present invention, described below, may be implemented in a variety of ways, such as a process, an apparatus, a system, a device, or a method on a tangible computer-readable medium.

Components, or modules, shown in diagrams are illustrative of exemplary embodiments of the invention and are meant to avoid obscuring the invention. It shall also be understood that throughout this discussion that components may be described as separate functional units, which may comprise sub-units, but those skilled in the art will recognize that various components, or portions thereof, may be divided into separate components or may be integrated together, including integrated within a single system or component. It should be noted that functions or operations discussed herein may be implemented as components. Components may be implemented in software, hardware, or a combination thereof.

Furthermore, connections between components or systems within the figures are not intended to be limited to direct connections. Rather, data between these components may be modified, re-formatted, or otherwise changed by intermediary components. Also, additional or fewer connections may be used. It shall also be noted that the terms "coupled," "connected," or "communicatively coupled" shall be understood to include direct connections, indirect connections through one or more intermediary devices, and wireless connections.

Reference in the specification to "one embodiment," "preferred embodiment," "an embodiment," or "embodiments" means that a particular feature, structure, characteristic, or function described in connection with the embodiment is included in at least one embodiment of the invention and may be in more than one embodiment. Also, the appearances of the above-noted phrases in various places in the specification are not necessarily all referring to the same embodiment or embodiments.

The use of certain terms in various places in the specification is for illustration and should not be construed as limiting. A service, function, or resource is not limited to a single service, function, or resource; usage of these terms may refer to a grouping of related services, functions, or resources, which may be distributed or aggregated. Furthermore, the use of memory, database, information base, data store, tables, hardware, and the like may be used herein to refer to system component or components into which information may be entered or otherwise recorded.

Furthermore, it shall be noted that: (1) certain steps may optionally be performed; (2) steps may not be limited to the specific order set forth herein; (3) certain steps may be performed in different orders; and (4) certain steps may be done concurrently.

As used herein, the term "information source" refers to any source of information, e.g., the Internet. The term "element" shall be understood to mean any content comprised in an information source or any content derived from an information source. The term "symptom-disease pair" refers to a co-occurrence of a symptom element and a disease element in a same source that may be used to indicate a relatedness between the terms symptom and disease. The terms "trustworthiness score" and "reliability score" are used interchangeably herein. The term "information trustworthiness" refers to a representation (e.g., a score) for the trustworthiness of information.

While symptom-disease relationships are used as examples herein, this is not intended as a limitation, as embodiments of the present disclosure may be equally applied to other relationships and pairings.

FIG. 1 illustrates an exemplary system for estimating a strength of a relationship between elements, according to various embodiments of the present disclosure. FIG. 1, as depicted, comprises one or more information sources 102, data processor 120, and scorer 132. In embodiments, data processor 120 comprises source reliability estimator 122 and information integrator 124.

Information sources 102 are online and/or offline sources that may comprise structured or semi-structured data. In embodiments, information sources 102 comprise co-occurring symptom and disease-related data 118 that may be used to extract medical knowledge. For example, based on given set of symptoms, a possible disease may be inferred by considering the relatedness of co-occurring data 118. It is understood that the level of trustworthiness of the information provided may vary between information sources 102.

In embodiments, data processor 120 receives symptom and disease data 118, for example, via a search processor (not shown) that searches information sources 102 to extract symptom and disease data 118 from semi-structured data. In embodiments, data processor 120 uses symptom and disease data 118 to calculate trustworthiness scores that indicate the strength of relationships between pairs of co-occurring terms. In embodiments, data processor 120 estimates the reliability of a particular source 110 based on a number of factors that may include the trustworthiness of information provided by source 110, an absolute or relative amount of information provided by source 110, and/or indicia of copying between sources 102. For example, if source 110 provides a certain number of pairs that have a similar low trustworthiness score as pairs provided by another source 112, source reliability estimator 122 may determine that both sources 110, 112 have low trustworthiness and, accordingly, decrease the trustworthiness scores for both sources 110, 112.

In embodiments, data processor 120 uses information integrator 124 to find information sources that comprise a particular symptom-disease pair and normalizes trustworthiness scores across those information sources that comprise the pair, such that the sum of the trustworthiness scores of all possible symptoms for a particular disease equals 1.

In embodiments, source reliability estimator 122 takes into consideration that the reliability of information source 110 may depend on the trustworthiness of the symptom-disease pairs information source 110 holds, and that the trustworthiness of each symptom-disease pair may depend on the trustworthiness of information source 110 that contains the pair. Therefore, in embodiments, data processor 120 employs an iterative weighted voting process wherein the weights are source expertise scores to estimate the reliability of information source 102 and calculate a trustworthiness score for symptom-disease pair. Each symptom-disease pair indicates the relationship between a symptom and a disease. In embodiments, the iterative process iterates the calculation of information source reliability and symptom-disease trustworthiness scores until the calculation converges or is stopped. In embodiments, data processor 120 uses a gradient descent processing method that takes advantage of fast convergence from initial to final values, while minimizing an estimation error of an objective function. Details of an exemplary iterative process are discussed further below, with respect to FIG. 3.

It is noted that while symptom-disease relationships are used as examples in FIG. 1, embodiments of the present disclosure may be equally applied to other relationships, e.g., relationships in a family tree.

One of ordinary skill in the art will appreciate that data processor 120 may comprise additional components, such as memory devices, not shown in FIG. 1.

Figure 2:
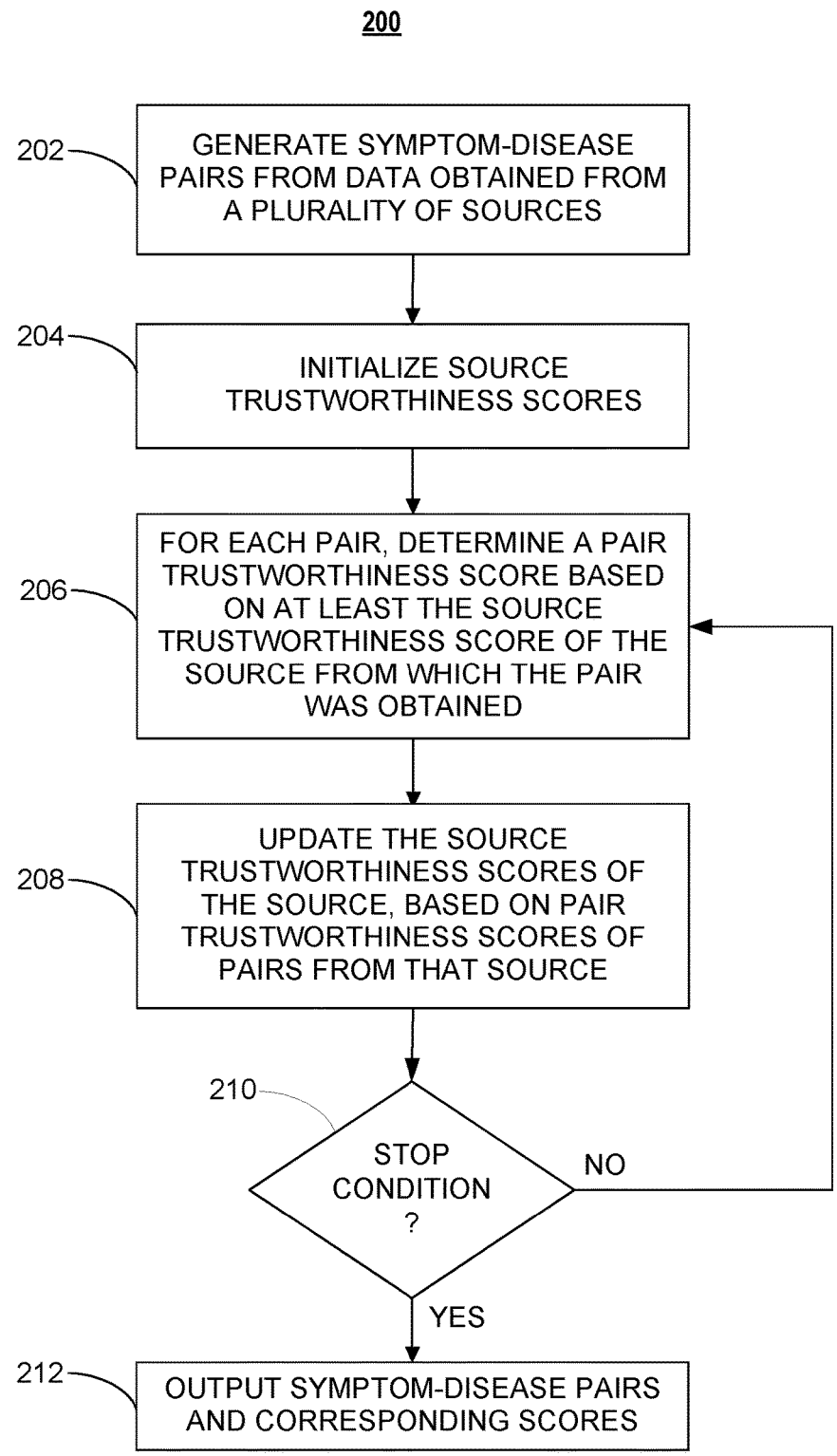
FIG. 2 is a flowchart that illustrates a process for estimating a strength of a relationship between elements, according to various embodiments of the present disclosure.

FIG. 2 is a flowchart that illustrates a process for estimating a strength of a relationship between elements, according to various embodiments of the present disclosure. The process for estimation process begins at step 202, when elements, such as symptom and co-occurring disease terms, are extracted from a plurality of sources to generate element-element pairs, e.g., symptom-disease pairs.

At step 204, the trustworthiness scores of one or more sources that comprise the elements, e.g., symptoms and corresponding diseases are initialized, before process 200 enters an iteration at step 206.

At step 206, for each element-element pair (e.g., symptom-disease pair), a pair trustworthiness score is determined based on at least the source trustworthiness score for the source from which the symptom was obtained. In embodiments, source trustworthiness score is a source expertise score that is used as weight in a voting process.

At step 208, the source trustworthiness scores of the source is updated, based on pair trustworthiness scores of pairs from that source.

At step 210 it is determined whether a stop condition has been reached. If not, process 200 returns to step 206 to continue with the iteration steps.

If process 200 determines, at step 210, that a stop condition has been reached, then, at step 212, element-element pairs and corresponding scores are output.

Figure 3:
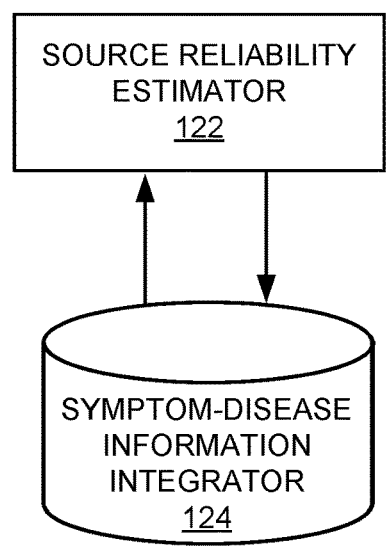
FIG. 3 illustrates an exemplary data processor for iteratively estimating a strength of a relationship between elements, according to various embodiments of the present disclosure.

FIG. 3 illustrates an exemplary data processor for iteratively estimating a strength of a relationship between elements, according to various embodiments of the present disclosure. Data processor 300 comprises source reliability estimator 122 and information integrator 124. In embodiments, since both symptom trustworthiness and the expertise of an information source (not shown in FIG. 3) are unknown, in embodiments, the trustworthiness of symptoms and the source expertise are jointly estimated.

In detail, in embodiments, given a set of disease terms Q and a set of sources $\mathcal{D}$ that provide co-occurring symptoms, assuming that $x_q^d$ denotes the symptom, x, for the q-th disease provided by the d-th source and $w_d$ denotes the expertise score of the d-th source, a weighted aggregation may be performed on the data $\{x_q^d\}_{q \in Q}, d \in \mathcal{D}$ to derive knowledge triples <disease, symptom, trustworthiness degree> and estimate source expertise scores. In embodiments, if a symptom is provided by one or more sources that have a relatively high expertise score, that symptom may be regarded as trustworthy. Similarly, if a source comprises numerous trustworthy symptoms, it may be assigned a relatively high expertise score.

In embodiments, the trustworthiness of symptoms and source expertise are iteratively updated as follows: In a first step, the degree of trustworthiness of a possible symptom, $x_q$, being related to the q-th disease is estimated as:

$$T(x_q) = \sum_{d \in \mathcal{D}} w_d \cdot \Pi(w_d, x_q^d), \qquad \text{Eq. (1)}$$

where $\Pi(\cdot, \cdot)$ represents an indicator function. $\Pi(x,y)=1$ for $x=y$ and $\Pi(x,y)=0$ for $x \neq y$, such that sources that do not comprise the symptom receive no weight. In embodiments, Eq. (1) may be formulated based on the following principle: the trustworthiness degree of a symptom is determined by the expertise scores of sources that provide that symptom for a given disease, such that high expertise score sources that comprise the symptom are considered more trustworthy than sources having lower expertise scores; i.e., a high source expertise score $w_d$ corresponds to a high degree of symptom trustworthiness $T(x_q)$.

In embodiments, trustworthiness degrees are normalized such that the sum of the trustworthiness degrees of all possible symptoms for a particular disease equals 1. As a result, $T(x_q)$ may be interpreted as the probability that symptom $x_q$ is trustworthy.

In embodiments, in a second step, the source expertise score is updated as follows:

$$w_d = -\log\left(1 - \frac{\sum_{x \in V_d} T(x)}{|V_d|}\right) \qquad \text{Eq. (2)}$$

where $V_d$ is the set of symptoms provided by the d-th source. Eq. (2) may be formulated based on the following principle: a higher expertise score is assigned to a source that provides relatively more trustworthy symptoms. In Eq. (2), the term $$\frac{\sum_{x \in V_d} T(x)}{|V_d|}$$

represents the average trustworthiness degree of the d-th source's symptoms, such that $$1 - \frac{\sum_{x \in V_d} T(x)}{|V_d|}$$

may be viewed as the probability of the d-th source providing wrong symptoms.

In embodiments, a logarithmic function is used to re-scale the source expertise scores such that the differences between the scores are enlarged. From Eq. (2), it can be seen that a source that is more likely to provide wrong symptoms receives a relatively lower expertise score.

In embodiments, the amount of information provided by a source is taken into consideration by using a pseudo count, $C_{pseudo}$, that is added to each source when estimating the expertise score for that source:

$$w_d = -\log\left(1 - \frac{\sum_{x \in V_d} T(x)}{|V_d| + C_{pseudo}}\right). \qquad \text{Eq. (3)}$$

According to this equation, if a source provides relatively few answers, $C_{pseudo}$, will dominate the term $|V_d|+C_{pseudo}$ such that the source expertise score will be relatively low. Conversely, if a source provides relatively answers to a relatively high number of diseases, $|V_d|$ will dominate the term $|V_d|+C_{pseudo}$, such that the source expertise score will be close to the original estimation.

In short, Eq. (1) estimates the trustworthiness degree for each possible symptom by conducting weighted voting wherein the weights are source expertise scores, and Eq. (3) updates the expertise score for each source based on the symptom trustworthiness degrees.

In embodiments, the source reliability estimator 122 uses a process that begins with an initialization, e.g., a uniform initialization, of source expertise scores prior to iteratively estimating symptom trustworthiness degrees and updating source expertise scores. The process may end when a stopping condition is met, e.g., when a solution to an objective function comprising Eq. (1) and Eq. (2) converges; the objective function reaches an acceptable level of error; or after a predefined number of iterations.

Figure 4:
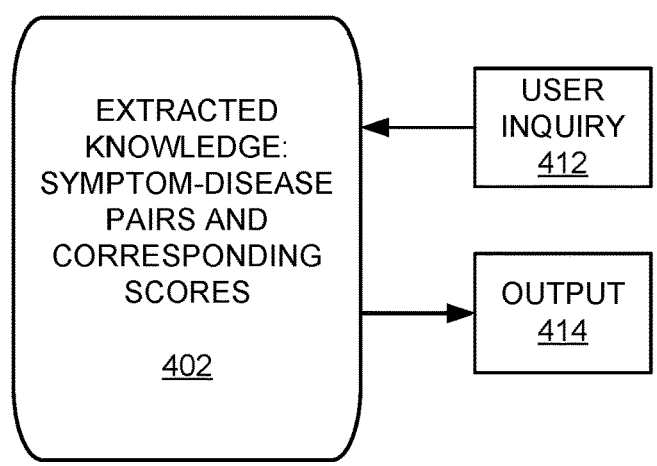
FIG. 4 illustrates an exemplary system for identifying one or more elements that are potentially related to a query element, according to various embodiments of the present disclosure.

FIG. 4 illustrates an exemplary system for identifying one or more elements that are potentially related to a query element, according to various embodiments of the present disclosure. System 400 comprises scorer 402 that, in embodiments, generates output 414 as a response to receiving user inquiry 412. While scorer 402 may be the same as shown in FIG. 1 and FIG. 4, this is not intended as a limitation. In embodiments, scorer 402 comprises an interface to interface with users via any method of communication known in the art. It is understood that scorer 402 may be integrated, for example, into the data processor shown in FIG. 1.

In embodiments, scorer 402 receives user inquiry 412, for example, in form of a query or a request that comprises one or more symptoms for which a user seeks matching diseases. In embodiments, scorer 402 uses an objective function to identify element-element pairs and corresponding pair trustworthiness scores that indicate the strengths of a relationship between the query term that is used in a source document and corresponding term used in the same source document. In embodiments, the objective function may be used to iteratively determine trustworthiness scores for symptom-disease pairs based on data from various information sources comprising co-occurring symptom and disease terms.

In embodiments, scorer 402 assigns scores, e.g., probability values, to the trustworthiness scores to indicate a relationship between symptoms provided by user inquiry 412 and matching diseases. In embodiments, scorer 402 outputs 414 the pair trustworthiness scores, (e.g., as probability values) that meet or exceed a threshold value.

In embodiments, output 414 combines at least two of symptoms, diseases, and a trustworthiness score that represents a relation between a symptom and a disease. In embodiments, output 414 may be used to generate a knowledge graph, for example, a graph in which nodes (e.g., nodes having uniform values) represent symptom and diseases, and weighted edges between a symptom and disease node represent a relation between the symptom and the corresponding diseases, such that the weighting of an edge corresponds to a symptom-disease pair trustworthiness score. It will be understood that output 414 may be used to generate any other representation of trustworthiness scores and information derived therefrom.

Figure 5:
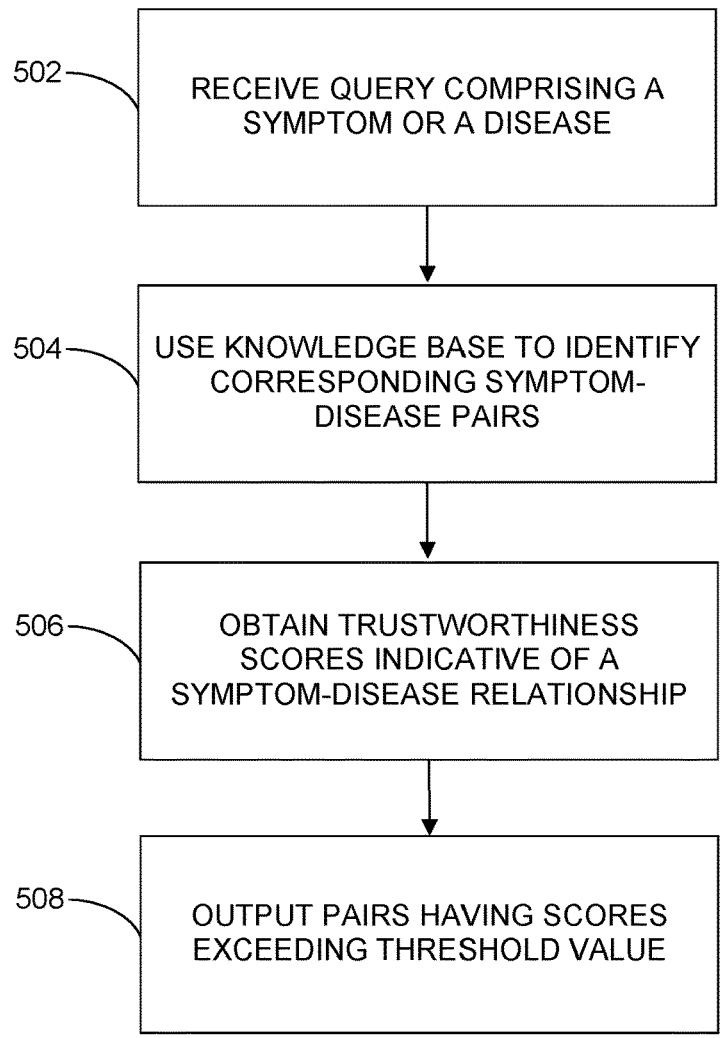
FIG. 5 is a flowchart that illustrates a process for identifying one or more elements that are potentially related to a query element, according to various embodiments of the present disclosure.

FIG. 5 is a flowchart that illustrates a process for identifying one or more elements that are potentially related to a query element, according to various embodiments of the present disclosure. The process for identifying elements begins, at step 502, when a query comprising at least one element is received, e.g., a user query that comprises one or more symptoms or diseases.

At step 504, process 500 uses a knowledge base to identify element-element pairs, e.g., symptom-disease pairs, corresponding to the element in the user query, e.g., a symptom. The symptom-disease pairs may have been generated based on data obtained from a plurality of sources, for example, by system 100 in FIG. 1.

At step 506, process 500 uses the knowledge base to identify pair trustworthiness scores corresponding to the element in the user query. In embodiments, the pairs and trustworthiness scores may be used to obtain probability values that indicate the strengths of a relationship between elements, e.g., a symptom-disease pair trustworthiness score for a symptom and a disease.

Finally, at step 508, process 500 outputs at least the pairs having scores and/or probability values that meet a threshold condition, for example, in the form of a <disease, symptom, trustworthiness degree> triple.

Figure 6:
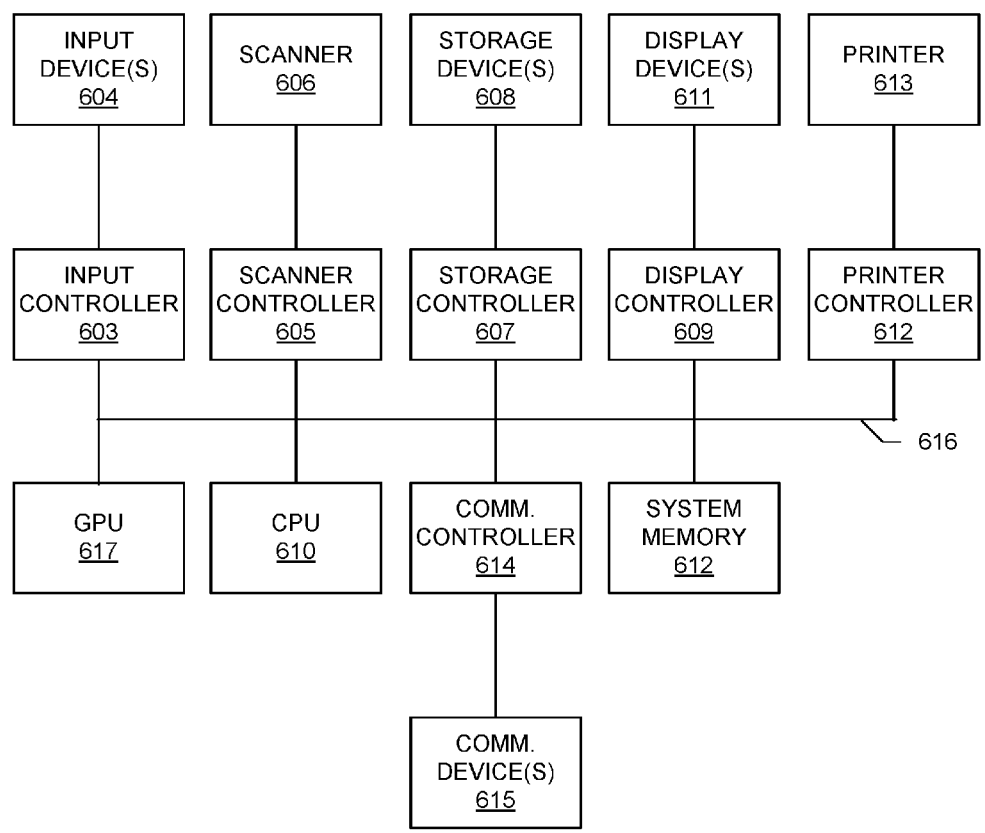
FIG. 6 depicts a simplified block diagram of a computing device/information handling system, in accordance with embodiments of the present disclosure.

FIG. 6 depicts a simplified block diagram of a computing device/information handling system, in accordance with embodiments of the present disclosure. It will be understood that the functionalities shown for system 600 may operate to support various embodiments of an information handling system—although it shall be understood that an information handling system may be differently configured and include different components.

As illustrated in FIG. 6, system 600 includes a central processing unit (CPU) 601 that provides computing resources and controls the computer. CPU 601 may be implemented with a microprocessor or the like, and may also include a graphics processor and/or a floating point coprocessor for mathematical computations. System 600 may also include a system memory 602, which may be in the form of random-access memory (RAM) and read-only memory (ROM).

A number of controllers and peripheral devices may also be provided, as shown in FIG. 6. An input controller 603 represents an interface to various input device(s) 604, such as a keyboard, mouse, or stylus. There may also be a scanner controller 605, which communicates with a scanner 606. System 600 may also include a storage controller 607 for interfacing with one or more storage devices 608 each of which includes a storage medium such as magnetic tape or disk, or an optical medium that might be used to record programs of instructions for operating systems, utilities and applications which may include embodiments of programs that implement various aspects of the present invention. Storage device(s) 608 may also be used to store processed data or data to be processed in accordance with the invention. System 600 may also include a display controller 609 for providing an interface to a display device 611, which may be a cathode ray tube (CRT), a thin film transistor (TFT) display, or other type of display. The computing system 600 may also include a printer controller 612 for communicating with a printer 613. A communications controller 614 may interface with one or more communication devices 615, which enables system 600 to connect to remote devices through any of a variety of networks including the Internet, an Ethernet cloud, a Fibre Channel over Ethernet (FcoE)/Data Center Bridging (DCB) cloud, a local area network (LAN), a wide area network (WAN), a storage area network (SAN) or through any suitable electromagnetic carrier signals including infrared signals.

In the illustrated system, all major system components may connect to a bus 616, which may represent more than one physical bus. However, various system components may or may not be in physical proximity to one another. For example, input data and/or output data may be remotely transmitted from one physical location to another. In addition, programs that implement various aspects of this invention may be accessed from a remote location (e.g., a server) over a network. Such data and/or programs may be conveyed through any of a variety of machine-readable medium including, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices.

Embodiments of the present invention may be encoded upon one or more non-transitory computer-readable media with instructions for one or more processors or processing units to cause steps to be performed. It shall be noted that the one or more non-transitory computer-readable media shall include volatile and non-volatile memory. It shall be noted that alternative implementations are possible, including a hardware implementation or a software/hardware implementation. Hardware-implemented functions may be realized using ASIC(s), programmable arrays, digital signal processing circuitry, or the like. Accordingly, the "means" terms in any claims are intended to cover both software and hardware implementations. Similarly, the term "computer-readable medium or media" as used herein includes software and/or hardware having a program of instructions embodied thereon, or a combination thereof. With these implementation alternatives in mind, it is to be understood that the figures and accompanying description provide the functional information one skilled in the art would require to write program code (i.e., software) and/or to fabricate circuits (i.e., hardware) to perform the processing required.

It shall be noted that embodiments of the present invention may further relate to computer products with a non-transitory, tangible computer-readable medium that have computer code thereon for performing various computer-implemented operations. The media and computer code may be those specially designed and constructed for the purposes of the present invention, or they may be of the kind known or available to those having skill in the relevant arts. Examples of tangible computer-readable media include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter. Embodiments of the present invention may be implemented in whole or in part as machine-executable instructions that may be in program modules that are executed by a processing device. Examples of program modules include libraries, programs, routines, objects, components, and data structures. In distributed computing environments, program modules may be physically located in settings that are local, remote, or both.

One skilled in the art will recognize no computing system or programming language is critical to the practice of the present invention. One skilled in the art will also recognize that a number of the elements described above may be physically and/or functionally separated into sub-modules or combined together.

It shall be noted that elements of the claims, below, may be arranged differently including having multiple dependencies, configurations, and combinations. For example, in embodiments, the subject matter of various claims may be combined with other claims.

It will be appreciated to those skilled in the art that the examples and embodiments herein are exemplary and not limiting to the scope of the present invention. It is intended that all permutations, enhancements, equivalents, combinations, and improvements thereto that are apparent to those skilled in the art upon a reading of the current document are included within the true spirit and scope of the present invention.

What is claimed is:

1. A method for estimating a strength of a relationship between elements, the method comprising:
    initializing source expertise scores for sources that comprise a co-occurrence of at least one first element in a set of first elements and a second element;
    until a stop condition has been reached, performing an iteration comprising:
        for the second element, calculating trustworthiness scores for a first element in the set of first elements by combining source expertise scores of the sources that comprise a co-occurrence of the first element in the set of first elements and the second element;
        updating the source expertise score of at least one of the sources by using the trustworthiness scores for first elements from the set of first elements provided by that source to determine a metric related to an average trustworthiness degree of first elements from the set of first elements provided by the source; and
        outputting a final trustworthiness score for one or more first element-second element pairs.

2. The method of claim 1, wherein the first element is a symptom and the second element is a disease.

3. The method of claim 1, wherein the average trustworthiness degree is related to a number of first elements provided by the source and comprises a factor that adjusts the source expertise score according to the number of first elements provided by the source.

4. The method of claim 1, wherein the step of updating gauges a level of copying from one or more sources in a manner such that higher levels of detected copying cause a relatively lower weight be assigned to the source trustworthiness score.

5. The method of claim 1, further comprising rescaling the source expertise score of the source to enlarge differences among trustworthiness scores, rescaling comprising applying a logarithmic function to the probability that the first element provided by the source are not trustworthy.

6. The method of claim 1, wherein the step of calculating trustworthiness scores for the first element comprises assigning a greater weight to a trustworthiness score provided by a source having a greater source expertise score than a trustworthiness score provided by a source having a relatively lower source expertise score.

7. The method of claim 1, further comprising assigning a relatively greater weight to the source expertise score of a source that provides greater trustworthiness scores than a source that provides relatively lower trustworthiness scores.

8. The method of claim 1, wherein the stop condition comprises the source expertise score and the trustworthiness score converging.

9. A method for identifying one or more elements that are potentially related to a query element, the method comprising:
    receiving a query comprising an element;
    identifying, for the element, a corresponding element from element-element pairs (pairs) that have been generated based on data obtained from a plurality of sources that comprise one or more co-occurrences of the element and the corresponding element;
    obtaining, for the identified corresponding element, a pair trustworthiness score that has been generated based on at least a source expertise score of a source from which the pair was obtained;
    updating the source expertise scores of the source from which the pair was obtained by using the pair trustworthiness score to determine a metric related to an average trustworthiness degree comprising the element; and
    outputting pairs having pair trustworthiness scores that meet a threshold.

10. The method of claim 9, wherein the average trustworthiness degree is related to a number of elements provided by the source and comprises a factor that adjusts the source expertise score according to the number of elements provided by the source.

11. The method of claim 9, wherein the first element is a symptom, the corresponding element is a disease, and the plurality of sources comprise semi-structured data.

12. The method of claim 9, further comprising rescaling the source expertise score of the source from which the pair was obtained to enlarge differences among pair trustworthiness scores.

13. A system for identifying one or more elements that are potentially related to a query element, the system comprising:
    one or more processors; and
    a non-transitory computer-readable medium or media comprising one or more sequences of instructions which, when executed by at least one of the one or more processors, causes steps to be performed comprising:
    receiving a query comprising an element;
    identifying, for the element, a corresponding element from element-element pairs (pairs) that have been generated based on data obtained from a plurality of sources that comprise one or more co-occurrences of the element and the corresponding element;
    obtaining, for the identified corresponding element, a pair trustworthiness score that has been generated based on at least a source expertise score of a source from which the pair was obtained;
    updating the source expertise scores of the source from which the pair was obtained by using the pair trustworthiness score to determine a metric related to an average trustworthiness degree comprising the element; and
    outputting pairs having pair trustworthiness scores that meet a threshold.

14. The system of claim 13, wherein the element is a symptom and the corresponding element is a disease.

15. The system of claim 14, wherein the step of iterating comprises normalizing the pair trustworthiness scores such that each pair trustworthiness score corresponds to a probability of a symptom associated with a pair being related to a disease associated with the pair.

16. The system of claim 13, wherein the step of updating gauges a level of copying from one or more sources in a manner such that higher levels of detected copying cause a relatively lower weight be assigned to the source expertise score.

17. The system of claim 13, wherein the step of updating the source expertise score of the source comprises assigning to a source that provides a greater number of elements a higher source expertise score than a source that provides a lesser number of elements.

18. The system of claim 13, wherein the plurality of sources comprise semi-structured data.

19. The system of claim 13, further comprising assigning a greater weight to the pair trustworthiness score provided by a source with a greater source expertise score than the pair trustworthiness score provided by a source with a relatively lower source trustworthiness.

20. The system of claim 13, further comprising assigning a relatively greater weight to the source expertise score of a source that provides greater pair trustworthiness scores than a source that provides relatively lower pair trustworthiness scores.

* * * * *